US006188812B1

(12) United States Patent
Kao et al.

(10) Patent No.: US 6,188,812 B1
(45) Date of Patent: Feb. 13, 2001

(54) METHOD AND APPARATUS FOR ENHANCED EVANESCENT FLUORESCENCE AND COLOR FILTERING USING A HIGH REFRACTIVE INDEX THIN FILM COATING

(76) Inventors: Hung Pin Kao, 2124 Promontory Cir., San Ramon, CA (US) 94583; Joseph Schoeniger, 126 Echo Ave., Oakland, CA (US) 94611; Nancy Yang, 72 Bacon Ct., Lafayette, CA (US) 94549

(*) Notice: Under 35 U.S.C. 154(b), the term of this patent shall be extended for 0 days.

(21) Appl. No.: 09/238,473

(22) Filed: Jan. 28, 1999

Related U.S. Application Data

(60) Provisional application No. 60/098,792, filed on Sep. 1, 1998.

(51) Int. Cl.$^7$ .................................................. G02B 6/00
(52) U.S. Cl. ............................ 385/12; 356/128; 356/436
(58) Field of Search ............................ 385/12; 356/128, 356/432, 436, 243.1; 250/458.1

(56) References Cited

U.S. PATENT DOCUMENTS

| | | | |
|---|---|---|---|
| 4,654,532 | 3/1987 | Hirschfeld | 250/461 |
| 5,138,153 | 8/1992 | Gergely et al. | 250/227 |
| 5,494,798 | 2/1996 | Gerdt et al. | 435/6 |
| 5,517,313 | 5/1996 | Colvin, Jr. | 356/417 |
| 5,525,466 | 6/1996 | Slovacek et al. | 435/6 |
| 5,738,992 | 4/1998 | Cook et al. | . |
| 5,745,231 | 4/1998 | Groger et al. | 356/128 |
| 5,961,924 | * 10/1999 | Reichert et al. | 422/82.11 |
| 6,103,535 | * 8/2000 | Pilevar et al. | 436/518 |

OTHER PUBLICATIONS

Kao, H. Pin, Yang, N., Schoeniger, J.S., "Enhancement of evanescent fluorescence from fiber optic sensors by thin film sol–gel coatings" J. Opt. Soc Am. A, vol. 15, No. 8, Aug. 1998, pp. 2163–2171.

Kao, H. Pin, Schoeniger, J.S., "Hollow cylindrical waveguides for use as evanescent fluorescence–based sensors: effect of numerical aperature on collected signal" APPLIED OPTICS, vol. 36, No. 31, Nov. 1997, pp. 8199–8205.

Browne, C.A., Tarrant, D.H., Olteanu, M.S., Mullens, J.W., Chronister, E.L., "Intrinsic Sol–Gel Clad Fiber–Optic Sensors with Time–Resolved Detection". Anal. Chem., vol. 68, No. 14, Jul. 1996, pp. 2289–2295.

Brinker, C.J., Hurd, A.J., Schunk, P.R., Frye G.C., Ashley C.S., "Review of sol–gel thin film formation" J. Non–Crystalline Solids, v. 147&148, 1992, pp. 424–436.

Hansmann, D.R., Milanovich, F.P., Vurek, G.G., Walt, D.R., "Fiber Optic Medical and Fluorescent Sensors and Applications" PROGRESS IN MEDICAL OPTICS, Proceedings of, Los Angeles, CA SPIE vol. 1648, Jan. 1992, pp. 194–201.

(List continued on next page.)

Primary Examiner—Frank G. Font
Assistant Examiner—Layla G Lauchman
(74) Attorney, Agent, or Firm—Timothy P. Evans

(57) ABSTRACT

A technique for increasing the excitation and collection of evanescent fluorescence radiation emanating from a fiber optic sensor having a high refractive index ($n_r$), dielectric thin film coating has been disclosed and described. The invention comprises a clad optical fiber core whose cladding is removed on a distal end, the distal end coated with a thin, non-porous, titanium dioxide sol-gel coating. It has been shown that such a fiber will exhibit increased fluorescence coupling due in part by 1) increasing the intensity of the evanescent field at the fiber core surface by a constructive interference effect on the propagating light, and 2) increasing the depth of penetration of the field in the sample. The interference effect created by the thin film imposes a wavelength dependence on the collection of the fluorescence and also suggests a novel application of thin films for color filtering as well as increasing collected fluorescence in fiber sensors. Collected fluorescence radiation increased by up to 6-fold over that of a bare fused silica fiber having a numerical aperture (N.A.) of O.6.

30 Claims, 7 Drawing Sheets

OTHER PUBLICATIONS

Glass, T.R., Lackie, S., Hirschfeld, T., "Effect of numerical aperture on signal level incylindrical waveguide evanescent fluorsensors" APPLIED OPTICS, vol. 26, No. 11, Jun. 1987, pp. 2181–2187.

Hellen, E.H., Axelrod, D., "Fluorescence emission at dielectric and metal–film interfaces" J. Opt. Soc. Am., B, vol. 4, No. 3, Mar. 1987, p. 337350.

Andrade, J.D., Vanwagenen, R.A., Gregonis, D.E., Newby, K., Lin, J.–N., "Remote Fiber–Optic Biosensors Based on Evanescent–Excited Fluoro–Immunoassey: Concept and Progress" IEEE Trans. Electron Devices, vol. ED–32, No. 7, Jul. 1985, pp. 1175–1179.

Axelrod, D., Burghardt, T.P., Thompson, N.L., "Total Internal Reflection Fluorescence". Am. Rev. Biophys. Bioeng., vol. 13, 1984, pp. 247–268.

Brinker, C.J., Harrington, M.S., "Sol–Gel Derived Antireflective Coatings for Silicon" Solar Energy Materials, vol. 5, 1981, pp. 159–172.

Lee, E.–H., Benner R.E., Fenn, J.B., Chang, R.K., "Angular distribution of fluorescence from liquids and monodispersed spheres by evanescent wave excitation" Applied Optics, vol. 18, No. 6, Mar. 1979, p. 862–868.

Carniglia, C.K., Mandel, L. Drexhage, K.H., "Absorption and Emission of Evanescent Photons" J. Opt. Soc. Am., vol. 62, No. 4, Apr. 1972, pp. 479–486.

Ekins, R.P., "Competitive, Noncompetitive and Multi–Analyte Microspot Immunoassays" *Immunochemistry of Solid–Phase Immunoassay*, CRC Press, J.E. Butler, ed. chapt. 6, pp. 105–138.

* cited by examiner

METHOD AND APPARATUS FOR ENHANCED EVANESCENT FLUORESCENCE AND COLOR FILTERING USING A HIGH REFRACTIVE INDEX THIN FILM COATING

CROSS REFERENCE TO RELATED APPLICATIONS

The present application is related to co-pending provisional application Ser. No. 60/098,792, filed Sep. 1, 1998, entitled METHOD AND APPARATUS FOR ENHANCED EVANESCENT FLUORESCENCE AND COLOR FILTERING USING A HIGH REFRACTIVE INDEX THIN FILM COATING, from which priority is claimed under 35 USC §119(e).

STATEMENT OF GOVERNMENT INTEREST

This invention was made with Government support under contract no. DE-AC04-94AL85000 awarded by the U.S. Department of Energy to Sandia Corporation. The Government has certain rights in the invention.

BACKGROUND OF THE INVENTION

Fluorescence is a photochemical phenomenon during which a photon within a specific range of light wavelengths (excitation wavelengths) is absorbed by an indicator molecule, thereby exciting an electron to a higher energy state. When the excited electron decays back to its original ground state, the absorbed energy is released either radiatively as a second photon of light at a longer wavelength (emission wavelengths), or dissipated non-radiatively into the environment around the indicator molecule. Fluorescence is the release of this second, longer wavelength photon from the indicator molecule. The total time between absorption of the excitation photon and the fluorescence emission is typically on the order of $10^{-8}$ s for transitions involving visible light.

The phenomenon of fluorescence has been applied for many years to the field of chemical detection and identification of species. Many fluorescence-based chemical sensors indirectly detect the presence of an analyte using fluorescent compounds whose fluorescence properties change in response to changes in the concentration of the analyte. Alternatively, the competitive binding of the analyte to a receptor molecule versus binding by a fluorescent labeled analog of the analyte can be detected. Much effort has been expended developing sensors to detect the light response of fluorescing materials because the fluorescent light response may be vanishingly small and therefore difficult to detect.

A desirable format for fluorescence sensing is involves immobilizing an analyte-sensitive fluorescent compound to the surface of a waveguide and then introducing the treated surface into a solution containing a target analyte. Light having wavelengths known to excite the fluorescence of the immobilized compound is passed into the waveguide. The electromagnetic wave generated at the surface of the waveguide, known as the evanescent field, excites the very thin layer of the immobilized compound. The fluorescence response of the compound is then collected by the same waveguide and measured at a point distal to the excited layer.

Such optical interaction then permits one to assay a variety of chemical and biological materials. A number of such systems using internal total reflection spectroscopy for an assay are known and have been described, for example, in U.S. Pat. No. 4,133,639 which discloses a system that measures fluorescence induced by the optical interaction; in U.S. Pat. No. 4,050,895 which describes a system based on absorption of the evanescent wave by the analyte; in U.S. Pat. Nos. 5,738,992, and 5,525,466 which describes a system based on absorption of the evanescent wave by an indicator species immobilized at the surface of a waveguide; and in U.S. Pat. No. 4,447,546 which describes a fluorescence immunoassay system.

A popular geometry for such evanescent field sensors is the surface of the core of a fiber optic waveguide. Excitation light is collected and delivered to a distal portion of the fiber where the cladding has been removed to expose the surface of the core and on which a covalently bonded indicator species has been immobilized. Light introduced into the proximal end of the waveguide is totally internally reflected in the optically dense medium of the waveguide, and generates the evanescent wave at the surface of the exposed waveguide, which extends only a fraction of a wavelength into the test solution. This penetration, however, is sufficient to permit substantial optical interaction between the evanescent wave component and the immobilized indicator species with which the analyte in the test solution interacts. A small percentage of the emitted fluorescent light is coupled back into the trapped mode of the waveguide and measured at a proximal end of the fiber. Although this geometry offers many advantages such as small size and remote sensing capability, the collection of only a small part of the total excited fluorescent light limits the sensitivity and cost of this sensor design.

Although the use of a fine glass fiber as a waveguide offers several advantages such as small size and remote sensing, the amount of total excited light limits the sensitivity and cost of these sensors. To increase the efficiency of fluorescence collection, several approaches have been proposed. U.S. Pat. No. 4,654,532 which discloses a method for improving the numerical aperture of a fiber optic waveguide; and U.S. Pat. No. 5,138,153 discloses a fiber optic waveguide having a membrane coating. Another possible technique for increasing the percentage of collected fluorescence is the application of a thin metal film onto the surface of the core of an optical fiber. It has been shown that the fluorescence emitted beyond the supercritical angle at a planar metal-film-coated dielectric interface can be approximately 2–3 times greater than that for a bare dielectric surface. However, fluorescence excited close to the surface of the metal film is quenched, limiting the total amount of collectable fluorescence. What is needed, therefore, is a method for increasing the excitation and collection efficiency of fluorescence emission in a fiber optic waveguide which is both simple and inexpensive.

One possible method for increasing excited and collected fluorescence at a totally internally reflecting surface might be the application of a thin film having a high refractive index, $n_r$, to the surface of the fiber optic. Such a high $n_r$ film is postulated to increase the excitation and collection of fluorescence through the greater depth of penetration of the evanescent field and the enhancement of the evanescent field intensity.

SUMMARY OF THE INVENTION

The instant invention relates to fluorescence devices and more particularly to fluorescence sensors.

Accordingly, it is an object of the invention to provide an improved fluorescence sensor.

It is an object of the invention to provide a fluorescence sensor with improved optical efficiency and greatly increased sensitivity.

It is an object of the invention to provide a fluorescence sensor that may have any emission wavelengths and any detection wavelengths.

It is still another object of this invention to provide a fiber optical waveguide having a core and having a cladding layer surrounding said core, the cladding layer removed at a detection end, and a dielectric thin film layer applied to the cylindrical surface of the bare fiber core.

It is yet another object of this invention to provide a dielectric thin film that has a high refractive index.

It is yet another object of this invention to provide a dielectric thin film that is generally non-porous.

It is another object of this invention to provide a sol-gel process by which the dielectric thin film may be created. Those skilled in the art, however, will recognize that there are many processes by which high refractive index film may be deposited onto the optical fiber. Some of these may include deposition of the film from a vapor phase, deposition by implantation of materials directly into the fiber surface (as with ion implantation), by diffusive means, and by in situ polymerization or chemical reaction with the waveguide surface. The sol-gel process is illustrated, herein, due to its simplicity, cost and effectiveness. Applicants, however, do not wish or intend to limit the scope of their invention merely to a sol-gel process.

Still another object of this invention is to provide a sensor having a thin film layer covering the detection end or covering intermediate sections of the waveguide which are incorporated at regular or irregular intervals along the length of the waveguide back from the distal end.

Another object of the invention is to provide a thin film layer that is a generally non-porous dielectric thin film.

Yet a further object of this invention is to provide a method for filtering fluorescence emission light frequencies by providing an optical waveguide removing the waveguide cladding from a portion of the distal end or intermediate sections of the waveguide, applying a high index of refraction thin film coating to the waveguide core surface, and adjusting the thickness of said thin film based on an interference characteristic of said waveguide and a known frequency bandwidth of light so as to preferentially detect a specific frequency bandwidth of light.

These and other objects are realized by employing, for purposes of the present invention, a clad fiber core whose cladding is removed in one or more sections at or near a distal end of the fiber, the distal end coated with a thin, non-porous, dielectric thin film coating. It can then be shown that such a fiber will exhibit increased fluorescence coupling due in part by 1) increasing the intensity of the evanescent field at the fiber core surface by a constructive interference effect on the propagating light, and 2) increasing the depth of penetration of the field in the sample. The interference effect created by the thin film imposes a wavelength dependence on the collection of the fluorescence and also suggests a novel application of thin films for color filtering as well as increasing collected fluorescence in fiber sensors. The principles demonstrated by this technique is applicable to sensors having a cylindrical geometry, such as an optic fiber or the interior of a hollow capillary fiber, or to sensors based on a planar geometry, such as a glass slide.

Other objects of the present invention will in part be obvious and will in part appear hereinafter.

The invention accordingly comprises the apparatus possessing the construction, combination of elements and arrangement of parts, and the method comprising the several steps and relation and order of one or more of such steps with respect to the others, all of which are exemplified in the following detailed disclosure, and the scope of the application of which will be indicated in the claims.

DETAILED DESCRIPTION OF THE INVENTION

It will be understood by those skilled in the optical arts that the terms "wavelength" and "frequency," when used to describe electromagnetic radiation, may be used interchangeably. It also will be appreciated that the term "waveguide," as used herein, shall mean a transparent dielectric body, the body comprising a core wherein any optical path through said core incorporates at least one total internal reflection.

The invention disclosed herein is directed to the fiber optic sensor for exciting and collecting fluorescence emissions and particularly to a non-porous, titanium dioxide sol-gel film deposited onto a multimode optical fiber.

Sol-gel ceramic fabrication techniques have been used, in the past, in many optical devices to construct lightweight optics, porous coatings, and uniform, high $n_r$, dielectric thin films. The sols are relatively simple to synthesize, and sol-gel films can be applied to surfaces using dip coating or spin coating techniques. These prior art fiber sensors, however, have used sol-gel technology to increase the efficiency of collecting fluorescence emissions by taking advantage of the porous nature of certain types of sol-gels and have not used evanescent fields to excite fluorescence emissions; rather, the fluorescence has been excited and collected using the propagating fiber modes which traversed the sol-gel film. The instant invention utilizes the unique properties of thin, non-porous, dielectric films as a platform for establishing an evanescent field for excitation and as a conduit to collect and pass fluorescence emissions to an underlying waveguide.

Figure 1A:
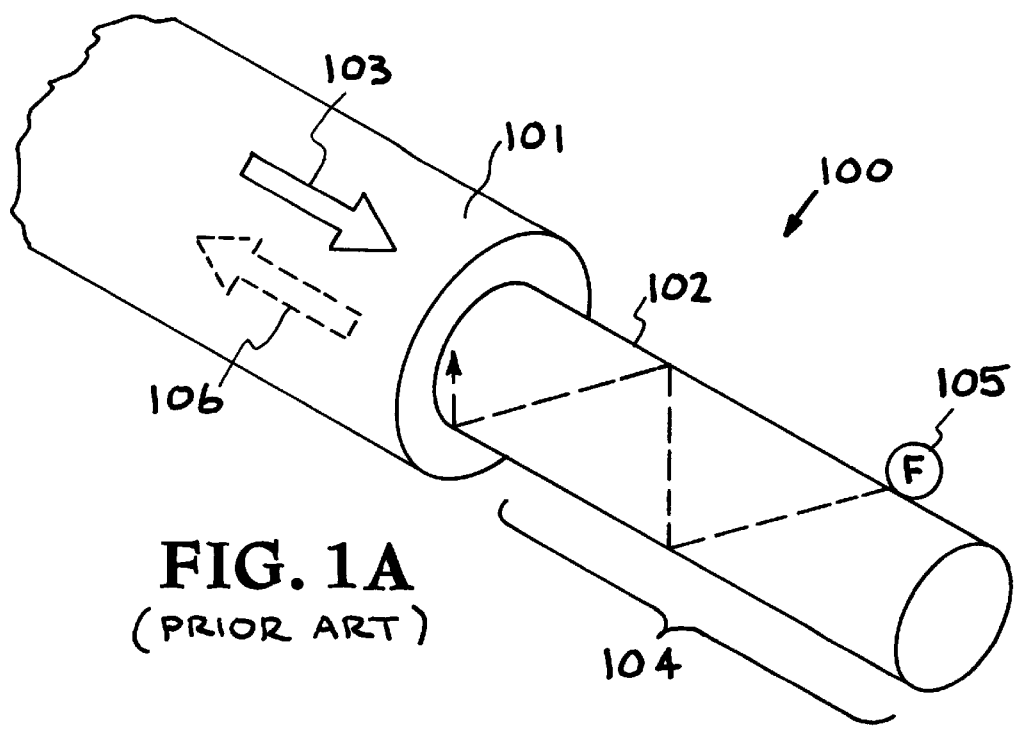
FIG. 1A illustrates the prior art structure of a fiber optic sensor having a bare, exposed detector end.
Figure 1B:
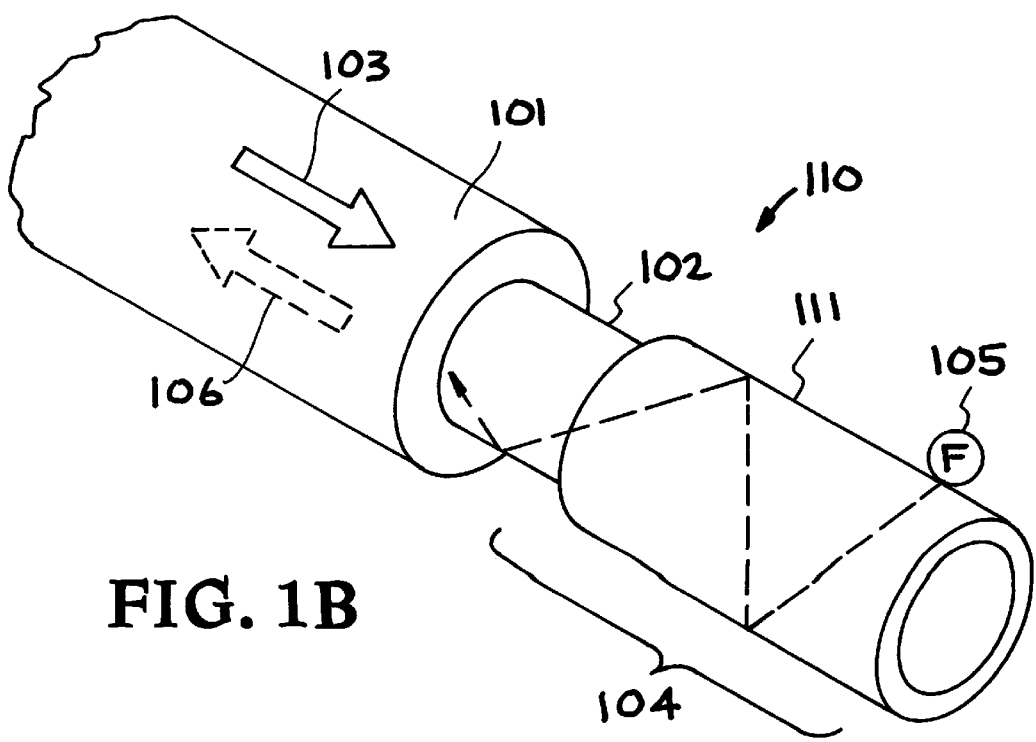
FIG. 1B illustrates the structure of a fiber optic sensor having a sol-gel, thin layer coating on a detector end.

A thin film optical fiber sensor has a structure similar to other conventional fiber optic sensors. The general structure is shown in FIG. 1. A conventional fiber optic sensor 100 is constructed by removing the cladding sheath material 101 thereby exposing the fiber core 102. Excitation light 103 is propagated to a distal end region 104 of the exposed core which is immersed into a unknown solution (not shown) containing a fluorophore 105. An evanescent field (not shown) arises along the cylindrical surface of the exposed core 102 due to the presence of the excitation light. This evanescent field excites the fluorescent molecules 105 at the core/solution interface which in turn emits its own characteristic wavelengths of radiation. Some of the fluorescence emitted by these molecules is coupled back into the fiber optic in propagating waveguide modes 106 and transmitted to the opposite end of the fiber (not shown) where it is detected.

For thin film fiber sensors 110, a thin film 111 is applied to the exposed core. The $n_r$ of the film is higher than that of the solution (usually water) and that of the fiber core. Because these films are intentionally very thin (on the order of a hundred nanometers) transmission modes which might otherwise exist and which would be confined only to the thin film are not present to any significant degree and, therefore, only a very small proportion of the total power represented in the emitted fluorescence light is propagated in these modes. The excitation and collection of fluorescence is predominately through modes which propagate along and across the fiber core 102, traverse the thin film and totally internally reflect at the thin film/solution interface. The effect of this thin film on the light collection efficiency of the fiber sensors as a function of numerical aperture (N.A.) of the excitation and collection optics has been calculated using a ray optics model for fiber sensors after T. R. Glass et al., and E. H. Lee, et al. The following recitation assumes a fiber optic having multiple modes, i.e., a fiber for which a very large number of propagating mode exist, and that the effect of transmission modes confined only in the thin film are negligible.

The level of fluorescence measured from a fiber optic, S, as a function of the numerical aperture (N.A.) of the optical system, is modeled as the product of three factors, $$S = kA_e E_c \quad (1)$$

where $A_e$ is proportional to the amount of power absorbed by the fluorescing molecules from the evanescent fields, where $E_c$ is proportional to the efficiency at which fluorescence is tunneled into the guided modes of the sensor, and where k is a proportionality constant incorporating factors independent of the system N.A., such as fluorophore concentration, and the spectral transmission of the detection optics. $A_e$ and $E_c$ may be calculated by integrating the effects of all rays entering the waveguide layer for a particular N.A. of the excitation and collection optics.

Figure 2:
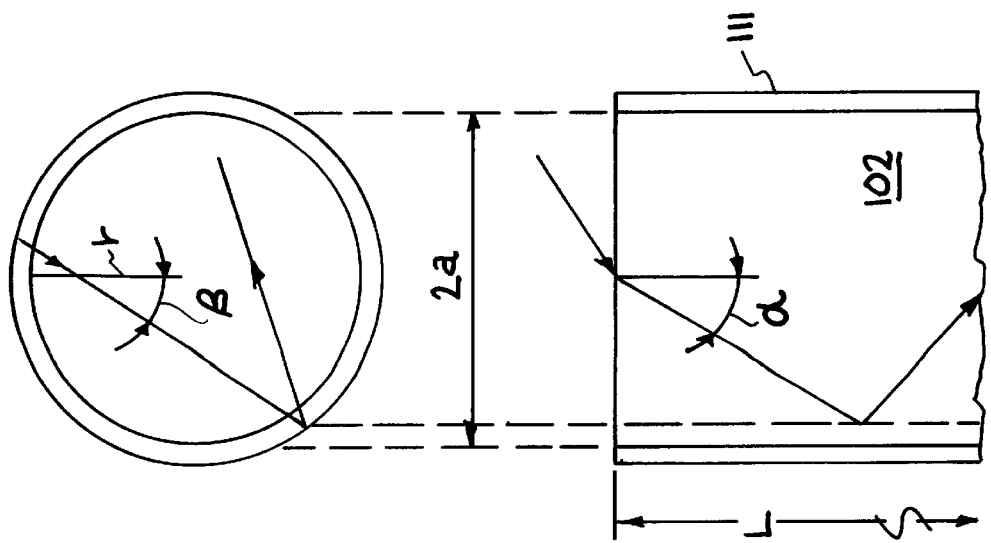
FIG. 2 shows a coordinate system for describing the path of a light ray in the fiber optic sensor.

For any particular ray, its contribution to $A_e$ and $E_c$ depends upon its optical path within the fiber. The path of each ray entering the fiber can be defined by four parameters based on its entry point into the waveguide: its distance, r, from the center of the waveguide where $0 \leq r \leq a$ and where a is the radius of the waveguide, an azimuthal angle $\beta$, a longitudinal angle $\alpha$, and the length of the waveguide, L (FIG. 2). The maximum longitudinal angle for the rays entering or leaving the fiber, $\alpha_{max}$ corresponds to the N.A. of the illumination/collection optics by N.A.=$n_{core}$ sin $\alpha_{max}$ where $n_{core}$ is the $n_r$ of the fiber core. All equations are derived in terms of $\alpha$ and related back to the N.A. by this equation. The total number of reflections, N(r$\alpha$, $\beta$), a particular ray undergoes as it travels down the fiber may be approximated by ignoring the distances traveled by the ray through the thin film. Hence, N(r, $\alpha$, $\beta$) reduces to the number of reflections for a ray propagating in a bare fiber, $$N(r, \alpha, \beta) = \frac{L \tan(\alpha)}{2a\sqrt{1 - \left[\left(\frac{r}{a}\right)\sin(\beta)\right]^2}} \quad (2)$$

where L is the total length of fiber coated with the film. The incident angle, $\eta$, which a particular ray makes at the fiber-film interface has been derived as, $$\cos(\eta) = \sin(\alpha)\sqrt{1 - \left[\left(\frac{r}{a}\right)\sin(\beta)\right]^2} \quad (3)$$

At all $\eta$, the ray will propagate through the thin film because it has a higher $n_r$ than the fiber. Because the film is very thin, the curvature of the fiber may be neglected when considering the propagation of the ray through the film. Hence, the film may be treated as a parallel plate and by Snell's Law, the incident angle of the ray at the film-sample interface is, $$\sin(\theta) = (n_{core}/n_{film}) \sin(\eta). \quad (4)$$

It is important to note that as the ray propagates down the fiber, the values of r, $\alpha$, $\beta$, $\eta$ and $\theta$ do not change (in the absence of scattering and mode mixing).

The magnitude of the evanescent field created by a ray totally internally reflecting at the film-sample interface is described by the transitivity, $T_{V,H}(\theta)$, for the electric field through the film, $$|T(\theta)|_V^2 = \frac{n_{sample}}{n_{core}} |t_V(\theta)|^2, \quad (5a)$$

$$|T(\theta)|_H^2 = \frac{n_{sample}}{n_{core}} |t_H(\theta)|^2 (\sin^2\theta' - \cos^2\theta') \quad (5b)$$

where the subscripts V and H refer to the vertical and horizontal polarization of the incident beam at the film-water interact and sin $(\theta') = (n_{film}/n_{sample})$ sin $(\theta)$. Note that the negative sign in the second term of equation (5b) results from the sum of the squares of the electric field components within the sample. The transmission coefficients, $t_V(\theta)$ and $t_H(\theta)$, have been derived for a three layer interface as, $$t_{V,H}(\theta) = \frac{t^{V,H}_{core-film}(\eta) t^{V,H}_{film-sample}(\theta) e^{i\left(\frac{2n_{film}h\pi\cos\theta}{\lambda}\right)}}{1 + r^{V,H}_{core-film}(\eta) r^{V,H}_{film-sample}(\theta) e^{i\left(\frac{4n_{film}h\pi\cos\theta}{\lambda}\right)}} \quad (6)$$

where $t^{V,H}$ and $r^{V,H}$ correspond to the transmission and reflection coefficients of the vertical and horizontal polarization at the single interface separating the specified two regions, h is the thickness of the film and I is the wavelength of light (either excitation or fluorescence) being considered. For randomly polarized light, as is the case for fiber sensors, the average of the two polarizations is used to describe the evanescent field, $$|T(\theta)|^2_{AVG} = \frac{n_{sample}}{2n_{core}}[|t_V(\theta)|^2 + |t_H(\theta)|^2(\sin^2\theta^2 - \cos^2\theta')] \quad (7)$$

The complete description of the evanescent field intensity includes a decaying exponential to describe the attenuation of the field in the sample, $$I_{evanescent} = |T(\theta)|^2_{AVG} e^{-2x/d_P} \quad (8)$$

where x is the distance from the totally internally reflecting surface, and, $$d_p = \frac{\lambda}{2\pi\sqrt{\sin^2\theta - \left(\frac{n_{sample}}{n_{film}}\right)^2}} \quad (9)$$

Note that equations (6), (7), and (8) reduce to the corresponding bare fiber (i.e., no thin film) equations by setting h=0 and $n_{film}=n_{core}$.

The total amount of power deposited in the sample depends upon $|T(\theta)|^2$AVG and $d_P$ of the evanescent field for each ray. The power deposited by a single ray having an incident angle of θ at the film-sample interface is found by integrating equation (8) from 0 to +∞. The power deposited by this single ray must be weighted by the umber of reflections it undergoes within the fiber N(r, α, β), and its incident power, $P_i$, onto the fiber face. If it is assumed that a Lambertian source is imaged onto the fiber optic face using well corrected optics, $P_i$=(r sin α, cos α). Thus, the total amount of power deposited into the sample $A_e$, is found by integrating over the power deposited by all the rays permitted to propagate within the fiber, $$A_e(\alpha_{max}) = \int_0^\theta \int_0^\infty N(r, \alpha, \beta) P_i |T(\theta)|^2_{AVG} e^{-2x/d_P} dx d\theta,$$

which is approximately, $$\int_0^{\alpha_{MAX}} \int_0^{2\pi} \int_0^a r \frac{\sin^2\alpha}{\sqrt{\left[1 - \left(\frac{r\sin\beta}{a}\right)^2\right]\left[\sin^2\theta - \left(\frac{n_{sample}}{n_{film}}\right)^2\right]}} |T(\theta)|^2_{AVG} dr d\beta d\alpha. \quad (10)$$

The total efficiency at which light is collected from the sample is found by invoking the principle of reciprocity. The principle of reciprocity states that the angular dependence of the fluorescence intensity at which light tunnels back into the waveguide is proportional to the angular dependence of the evanescent field intensity in the sample. Thus, the efficiency at which fluorescence is collected is proportional to the integral of the evanescent field intensities, $I_{evanescent}$, for all possible rays propagating within the fiber weighted by the number of reflections each ray makes within the fiber, N(r, α, β), $$E_c(\alpha_{MAX}) = \int_0^\theta \int_0^\infty N(r, \alpha, \beta) |T(\theta)|^2_{AVG} e^{(-2x/d_P)} dx d\theta$$

or approximately, $$\int_0^{\alpha_{MAX}} \int_0^{2\pi} \int_0^a r \frac{\tan\alpha}{\sqrt{\left[1 - \left(\frac{r\sin\beta}{a}\right)^2\right]\left[\sin^2\theta - \left(\frac{n_{sample}}{n_{film}}\right)^2\right]}} |T(\theta)|^2_{AVG} dr d\beta d\alpha. \quad (11)$$

Note that $A_e$ and $E_c$ are well approximated by the continuous integrals given by equations (10) and (11), respectively, rather than by discrete sums over all the modes because of the large number of modes carried by a multimode fiber.

It is important to note that the equations derived for both $A_e$ and $E_c$, given by equations (10) and (11) respectively, may also be used to compute the total collected fluorescence for different film thicknesses, different film refractive indices and the case of a bare fiber. Carniglia et al., derived the functional forms of the absorption and fluorescence emission by a dipole and, aside from a scaling factor, both the absorption and emission depend only upon intensity of the evanescent field as expressed by the Fresnel transmission coefficient at the film-sample interface. Hence, because both $A_e$ and $E_c$ were derived based on the intensity of the evanescent field through the thin film, these equations may be used to compute and compare the total collected fluorescence for different film optical properties and for a bare fiber.

The relative collected fluorescence at an N.A. corresponding to $\alpha_{max}$ was obtained by numerically integrating equation (10) for $A_e$ and equation (11) for $E_c$ and multiplying these two values together as in equation (1) to obtain S. For the calculation of equations (10) and (11), a single average wavelength is chosen for both the excitation and emission light.

EXAMPLES

Figure 3:
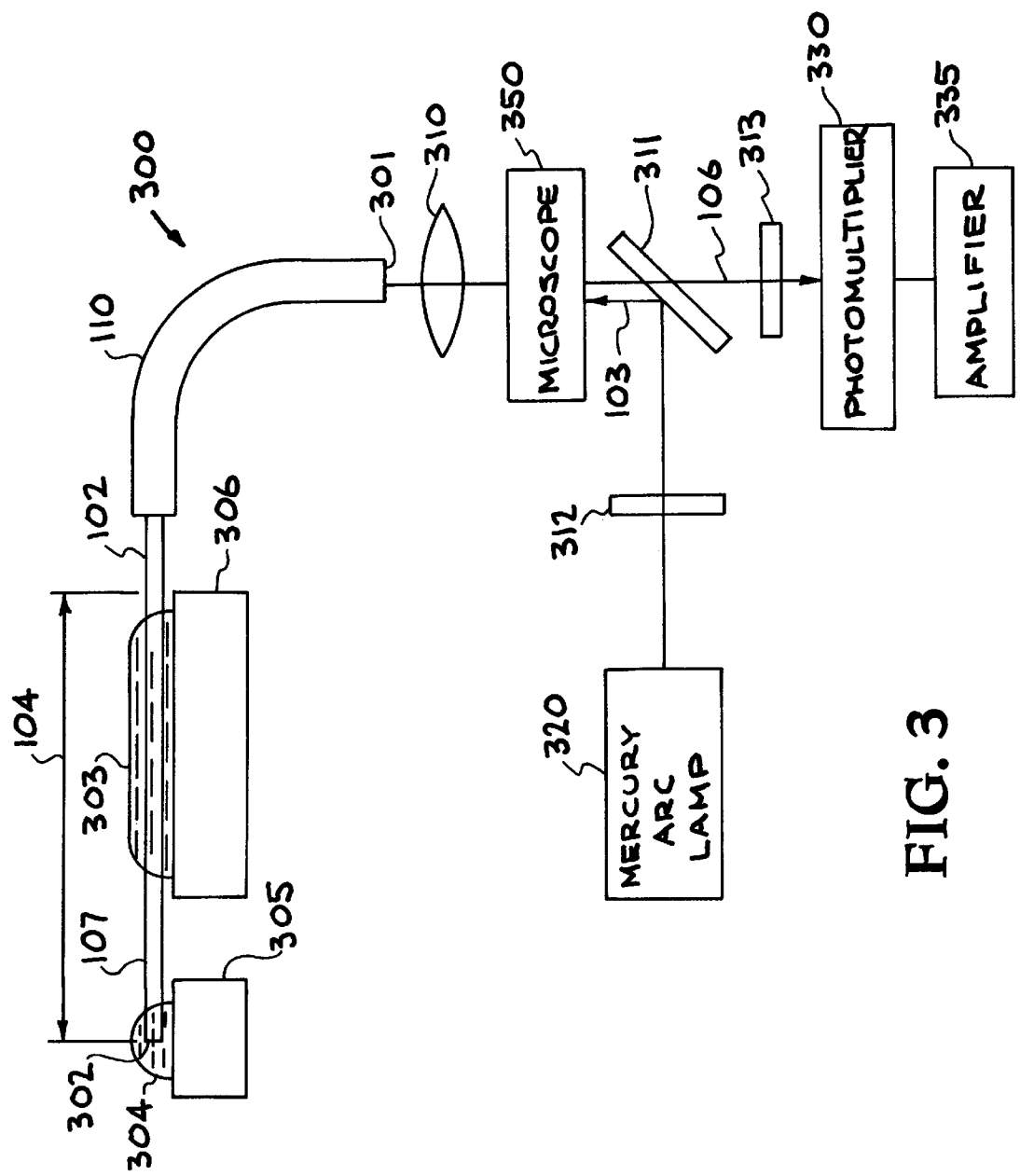
FIG. 3 provides a schematic of an epi-fluorescence optical configuration for excitation and collection of fluorescence.

In order to better explain the instant invention the following examples are provided. The experimental apparatus for measuring the evanescence signal for fiber sensors is shown in FIG. 3. Measurements were made with 4 different objectives 310 to achieve different excitation and emission optic numerical apertures (0.13, 0.24, 0.40, 0.60) on inverted epi-fluorescence microscope 350 (Olympus, IX70) and a 100 W mercury arc lamp 320. Light from arc lamp 320 was filtered through a 70 nm wide six-cavity interference filter 312 centered at 610 nm (Omega Optical Corporation, 610DF70) and reflected through dichroic mirror 311 centered at 640 nm (Omega Optical Corporation, 640DRLP) onto sample 303. Fluorescence light collected through objective lens 310 transmitted through dichroic mirror 311 and was filtered by a 40 nm wide six-cavity interference filter 313 centered at 690 nm (Omega Optical Corporation, 690DF40). The intensity of the fluorescence was detected by a red-enhanced photomultiplier 330 (Hamamatsu, R3896) operating at −625 V; the photomultiplier current was amplified using a current to voltage amplifier 335 (Stanford Research Systems, SR570) and measured using an A/D board (National Instruments, 1600CX) in a 486DX133 computer (not shown).

Optical fiber 110 used for all experiments had a 400 $\mu$m diameter fused silica core 102 and a 10 $\mu$m thick Teflon cladding layer to give an N.A. of 0.66 (Polymicro Technologies, FSU400420). Note that although the fiber has an N.A. of 0.66, the aqueous fluorescent sample 303 has a greater $n_r$ than Teflon. This reduced the maximum effective N.A. of the fiber sensor to 0.60. The total length of each fiber 110 measured was 1–1.2 m. Both ends of the fiber were cleaved with a cutting stone, and the Teflon cladding from the distal 7.5 cm of fiber was removed using a heated wire stripper. The distal portion 104 of each fiber was first cleaned and baked as described below, after which the fluorescence was measured for bare fiber core 102. Then, the sol gel thin film was created on the fiber surface, and the fluorescence readings were taken again.

Before any measurements, the distal bare fiber tip 302 was cleaned using a cotton-tipped applicator to apply deionized water, acetone and ethanol successively. The distal 6.5 cm of fiber 110 was then baked in a small tubular oven where the temperature was ramped up from room temperature to 430° C. over 7 minutes, held at this temperature for 8 minutes and then allowed to cool to room temperature over a period of 15 minutes. A thin film 111 was deposited on the fiber by inserting the distal 6 cm of bare fiber 102 into a titanium sol at a speed of 8 inches/minute, holding it submerged for 60 seconds, and removing the fiber at a speed of 8 inches/minute using a computer-controlled vertical translation stage. The applied sol layer 101 was allowed to dry at room temperature for 5 minutes, after which the distal 6.5 cm was baked again as described above. Additional sol layers were added by repeating the dip and bake process. Up to 20 successive sol layers were added by repeating the dip and bake process. The same preparation and dip procedures were followed for creating a single titanium sol gel coat on a glass cover slip (Fisher Scientific Company, Fisher Brand No. 1 Cover Slips). Details of the sol synthesis have been described in the prior art.

To measure the collected fluorescence 106, the proximal tip 301 of fiber 110 was mounted onto the fluorescence microscope 350 and was not moved throughout the entire experiment. Distal fiber tip 302 was immersed into the meniscus of a liquid 304 contained in a Teflon well 305. This liquid was a Series M standard Cargille reference liquid having a refractive index ($n_r$) of 1.78 (R.P. Cargille Laboratories, Inc., Refractive Index Series M) which effectively coupled nearly all the propagating radiation out of the fiber optic terminus 302. Background fluorescence readings were then measured at all 4 objective powers. Next, a second well 306 filled with a solution containing the fluorescent dye, hexamethylindodicarbocyanine iodide (Aldrich Chemical Company), dissolved at a concentration of 1 mg/ml in deionized water. The solution which has an excitation maximum at 635 nm, and an emission maximum at 655 nm, was placed such that about 5 cm of distal fiber portion 104 was immersed in the meniscus of the solution. Fluorescence readings were then measured at all 4 objective magnifications.

Figure 6A:
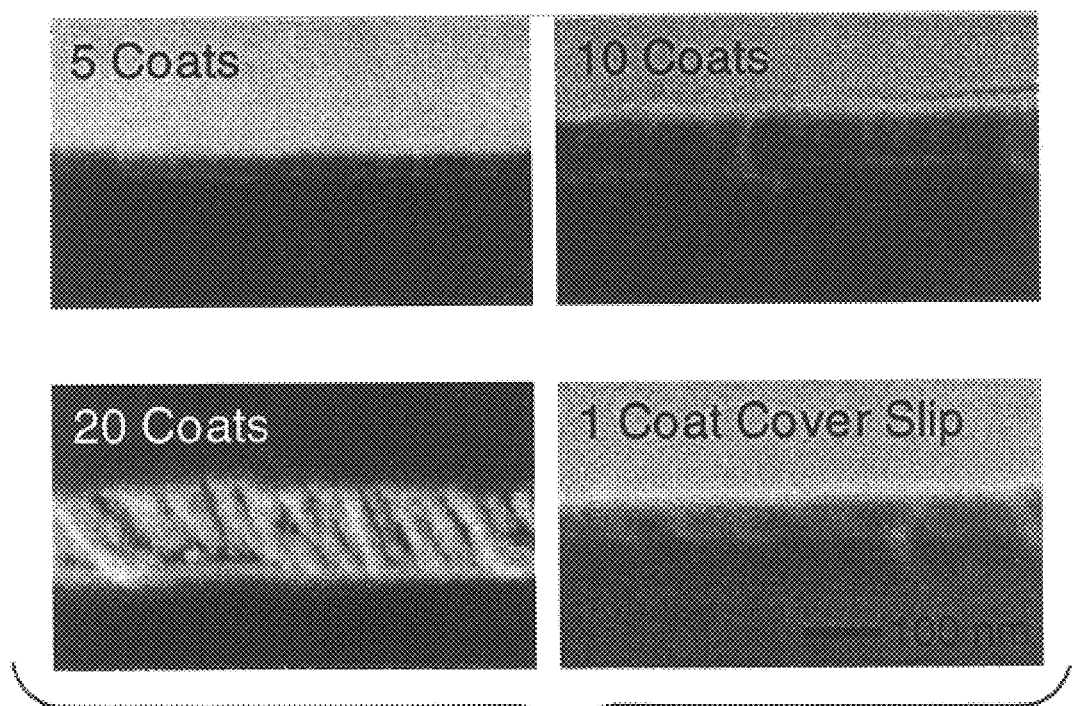
FIG. 6A illustrates examples of photomicrographs showing sol-gel thin films of varying thickness.

The thicknesses and microstructure of the titanium-dioxide thin films were determined using a field emission scanning electron microscope (FESEM) (JEOL Inc., Model JEOL 6400F). Film thicknesses were measured at a fresh fracture surface using an accelerating voltage of 1–2 kV and a magnification of approximately 100,000×. FESEM images were obtained for fibers having 5 10, 15, and 20 sol gel coatings (FIG. 6A). Thicknesses of fibers having less than 5 sol gel coatings were estimated from a linear least squares fit of the data measured for fibers having 5 and 10 coatings. The atomic structure of thin sections of the coated fiber was examined in bright field using a high resolution transmission electron microscope (HRTEM) (JEOL Inc., Model JEOL 4000) operating at an accelerating voltage of 400 kV. Thin sections of the film were created using ion beam milling. Titanium composition was determined using localized energy dispersive X-ray spectroscopy (EDX) using an acceleration voltage of 15 kV and an excitation volume of 1–2 $\mu$m spot diameter.

Numerical integration of equations (10) and (11) were performed using MATLAB for Windows 4.0. The integration was performed at seven $\alpha_{MAX}$ values between 0 and the maximum sensor NA. of 0.60. For the simulations, the $n_r$ of fused silica fiber core 102 and water were taken as 1.458 and 1.33 respectively. Collected fluorescence 106 was calculated as a function of film refractive index, film thickness, and fluorescence excitation and emission wavelengths.

Figure 4:
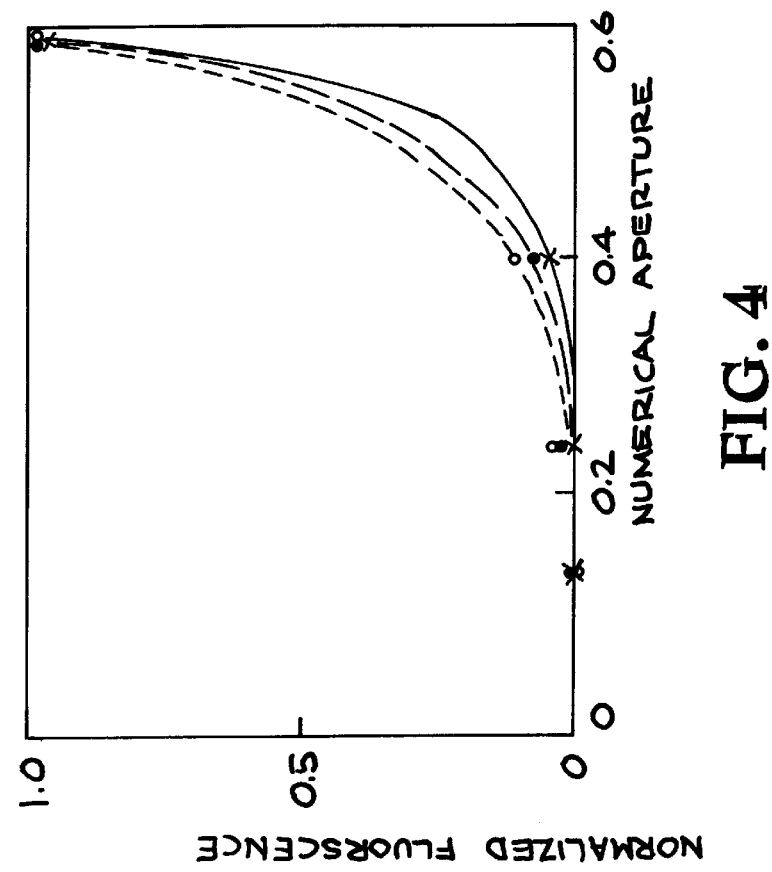
FIG. 4 illustrates the dependence of collected fluorescence on the excitation/collection optics numerical aperture (N.A.) for different film refractive indices and thickness. All data are normalized to the value measured for the sample at N.A.=0.6.
Figure 5A:
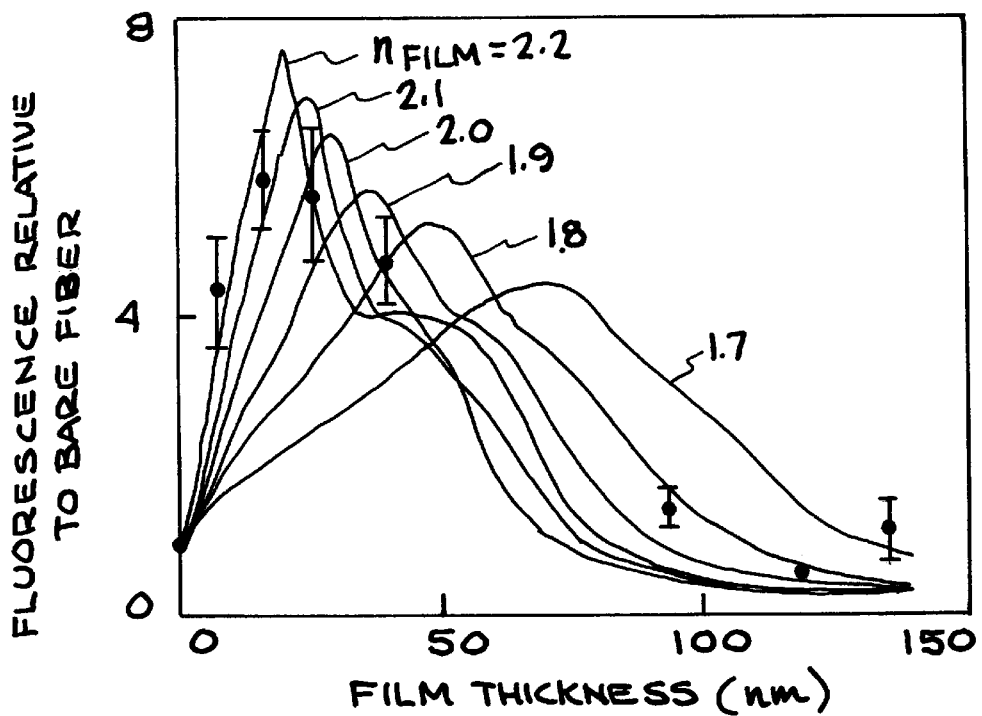
FIG. 5A illustrates the dependence of collected fluorescence on the film thickness and refractive index for samples at an N.A. of 0.4.
Figure 5B:
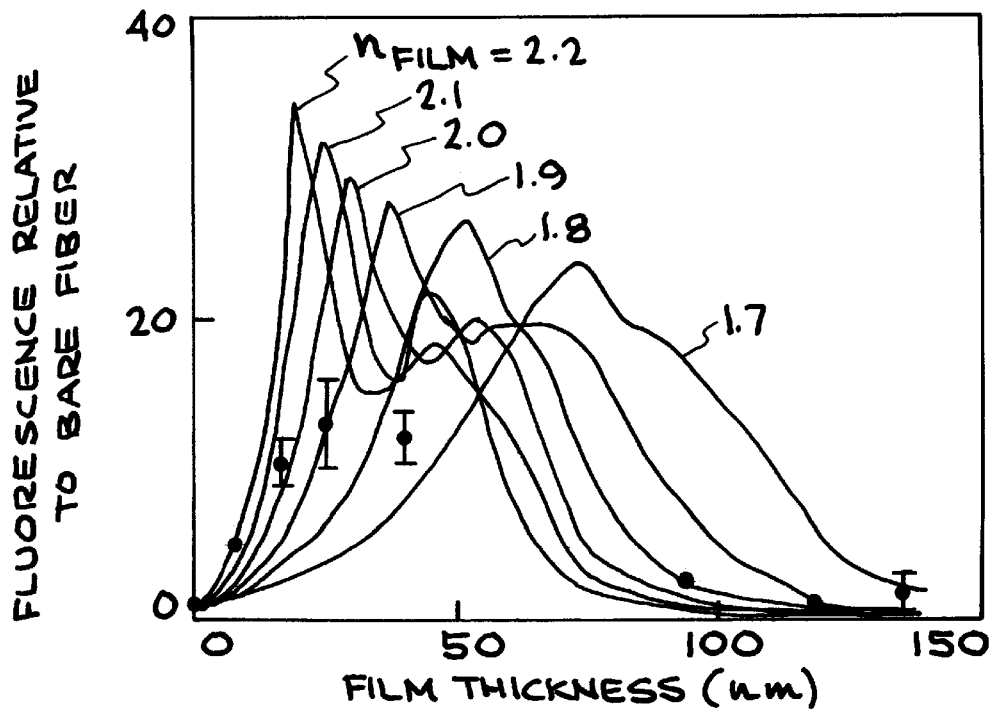
FIG. 5B illustrates the dependence of collected fluorescence on the film thickness and refractive index for samples at an N.A. of 0.6.

The numerical simulations predicted a strong dependence of the collected fluorescence 106 on the N.A. and the thickness of the thin film 111. As N.A. increased, the calculated fluorescence signal monotonically increased for a particular $n_r$ or thickness of the film 111 (FIG. 4). The maximum calculated fluorescence occurred at the sensor N.A. of 0.6. For a particular $n_{film}$ and N.A., fluorescence increased to a local maximum as the thickness of film 111 increased (FIG. 5A, & 5B). As film thickness increased further, the calculated fluorescence decreased to either a shoulder or second local maximum and eventually to a level below that of bare fiber 102. If $n_{film}$ increased, the first local maxim increased and shifted to smaller thicknesses (FIG. 5A, & 5B).

The experimental data were found to be in general agreement with the theoretically predicted data. At an N.A. of 0.6, collected fluorescence 106 increased to a local maximum and decreased to a level below that for bare fiber 102 as the thickness of film 111 increased (FIG. 5A). However although the numerical simulations demonstrate the same behavior, the experimental data were close but not coincident to any of the simulated curves for a single $n_{film}$. At an N.A of 0.4, the experimental data and numerical simulations are in qualitative, but not quantitative agreement. In agreement to the numerical simulations, collected fluorescence increased to a local maximum and decreased as the thickness of film 111 increased (FIG. 5B). Moreover, the ratio of the collected fluorescence 106 to that from bare fiber 102 is in general, greater at an N.A. of 0.4 than at an N.A. 0.6. However, unlike the response at an N.A. of 0.6, this data was not close to any of the simulated curves.

Figure 6B:
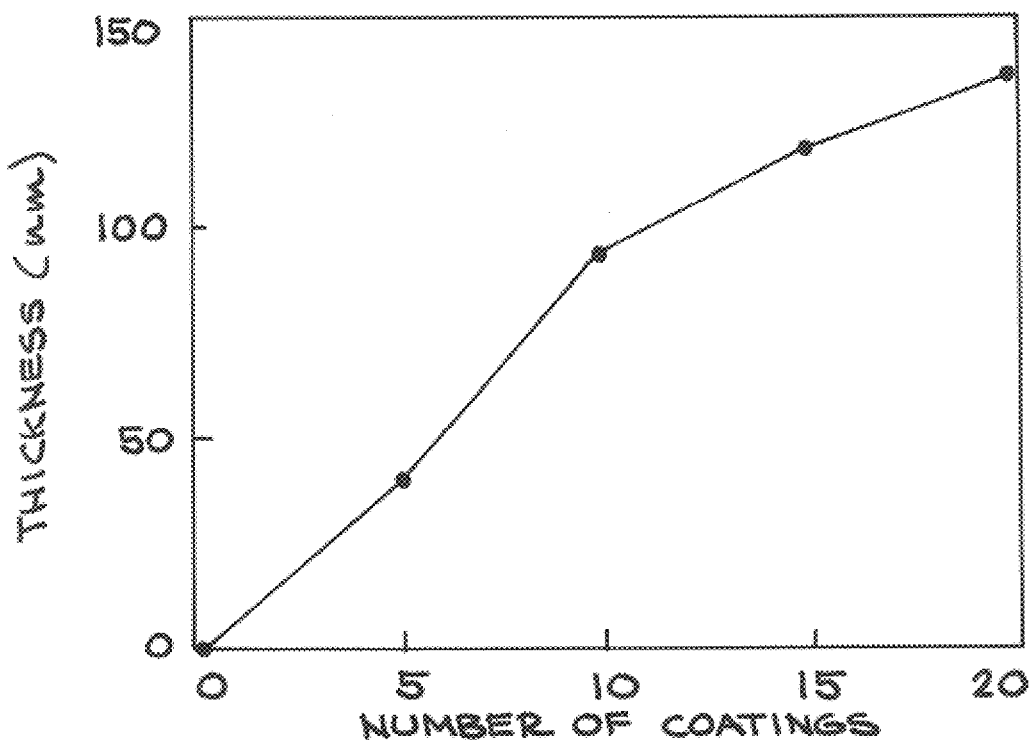
FIG. 6B illustrates the relationship between film thickness and number of coatings on the coated glass fiber.
Figure 7A:
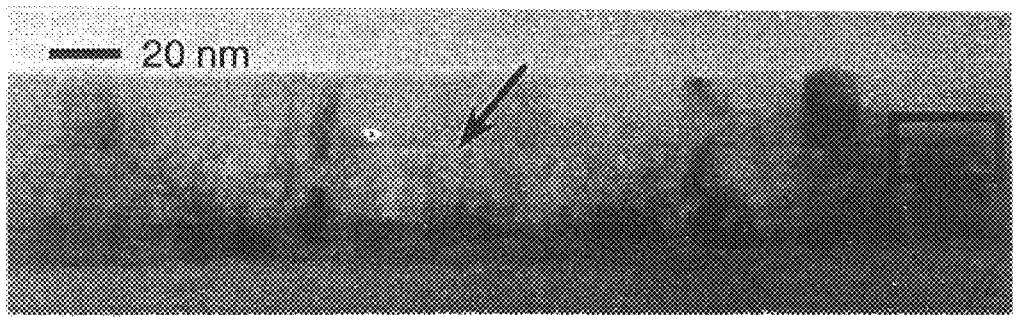
FIG. 7 illustrates the crystallinity and porosity of the sol-gel films.
Figure 7B:

The thickness and microstructure of the titanium sol gels formed on fiber optics is significantly different from those formed on planar glass surfaces. The thickness of the sol gels formed on fibers increased linearly with the number coatings up to 10 coatings, after which it began to plateau (FIG. 6A, & 6B). This increase in thickness was verified by EDX spectroscopy of the layers, which demonstrated an almost linear increase in titanium content of the fiber surface up to 10 coats (data not shown). For a sol gel film formed by a single dip coat on the fiber, the thickness was ≈7–8 nm. By contrast, the thickness of a single, dip-coated, sol gel film on a planar glass surface was ≈60–70 nm, in excellent agreement to the value of 66 nm measured previously by ellipsometry (FIG. 6A). It is possible that surface tension effects reduced the thickness of the wet sol deposited on the fiber, thereby reducing the eventual thickness of the cured sol gel film. The crystalline structure of fiber films is also significantly different from planar films. For fiber films, a crystalline, columnar structure was evident, whereas planar films appeared amorphous (FIG. 6A). HRTEM images verified the crystallinity of the fiber films and demonstrated the existence of micro-domains (FIG. 7A, & 7B). To our knowledge, this type of crystallinity has not been previously observed in titanium sol gel films.

The fiber films demonstrated no significant surface porosity. For a 10 coat fiber film, pores or voids become evident 2–5 nm from the fused silica-sol gel interface, but are absent from the outer half of the coating (FIG. 7A). Surface FESEM photomicrographs show no evidence of surface porosity (FIG. 7C), and demonstrate excellent surface quality (variation <10 nm) over the field of view. Further evidence that the pores are not contiguous with the surface of the films is provided from electron photomicrographs of a film surface which had been soaked in a 100 mM solution of cadmium chloride. These photomicrographs showed no evidence of any surface concentrations of cadmium by EDX spectroscopy (data not shown).

Both numerical simulations and experimental data show that the addition of a high $n_r$, thin film to the surface of a fused silica fiber sensor can significantly increase the level of collected evanescent fluorescence and is dependent upon the thickness of the film. This effect can be attributed to the greater $d_p$ of the evanescent field and the enhancement of the evanescent field intensity. For a thin film fiber, the $d_p$ for any ray propagating in the fused silica core and totally internally reflecting at the sample surface is increased relative to that for a bare fiber by $n_{film}/n_{core}$. Hence, from equations (1), (10) and (11), the increase in collected fluorescence will then be $(n_{film}/n_{core})^2 \approx 2.3$ (assuming $n_{film} \approx 2.2$ and $n_{core} \approx 1.46$). The effect of the higher $d_p$ is independent of both the incident angle of the ray and film thickness for a given $n_{film}$. The remainder of the increase in fluorescence arises from the enhancement of the evanescent field intensity resulting from interference effects of the propagating light within the film. These interference effects cause the collected fluorescence to vary as a function of the film thickness, and as would be expected, are wavelength dependent. This dependence is apparent from the positions of the local maxima of $A_e$ and $E_c$ as a function of film thickness, which do not coincide because of the Stokes shift of the fluorescent dye. Because of the difference of the positions of these maxima, a shoulder or a second local maximum is observed in the calculated collected fluorescence curves as the film thickness is increased (FIG. 5A, 5B).

The interference effects arise from the propagation of the light through the thin film, and the positions and magnitudes of the maxima are determined by the transmitted angles of the light into the film as well as the wavelengths of the propagating light. As $n_{film}$ increases, the range of transmitted angles over which the light rays from the fiber enter the film will decrease even though the range of incident angles remains the same (65.8° to 90°). For example, for $n_{film}=2.15$, the range of transmitted angles is 38.2° to 42.7° whereas for $n_{film}=1.7$, the range of angles is 51.5° to 59.1°. This narrow range of transmitted angles approximates the propagation of a light ray through a thin film and causes the interference effects observed in the fluorescence collection. If $n_{film}$ decreases, thereby causing the range of transmitted angles to increase, the light ray approximation weakens, and interference effects are not as strong (FIG. 5A, 5B). In addition, the lower $n_{film}$ is expected to increase the position of the first maxima (FIG. 5A, 5B). Conversely, it would be predicted that a greater $n_{film}$ would increase the gain at the first maxima and reduce the width of the maxima at a smaller film thickness, as suggested by the simulations in FIG. 5. Interference should also be strongly dependent upon wavelength, whose effect may be utilized to filter unwanted fluorescence signals in the fiber (see below).

Figure 7C:
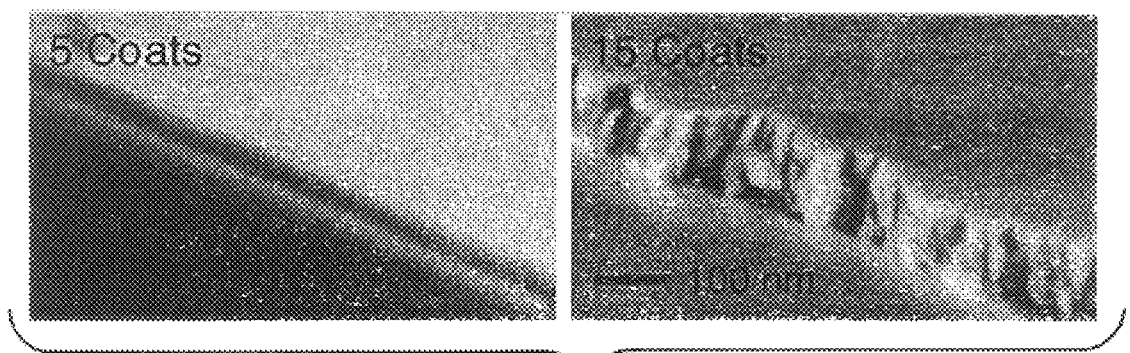

At the maximum fiber sensor N.A. of 0.6, both the experimental data and the simulations are in good agreement and predict increases in the collected fluorescence of up to 6× (FIG. 5A). However, at an N.A. of 0.4 (closer to the N.A. of standard communications fiber optics), the experimental data are consistently much lower than the simulations. Experimental data show increases of up to only 12× compared to the predicted increase of up to 35× (FIG. 5B). This discrepancy is most likely caused by mode mixing, which can be significant over small lengths of a fiber sensor. Mode mixing decreases the collected fluorescence at all N.A.'s, but the magnitude of the decrease becomes greater as N.A. is lowered. These lower N.A.'s have greater losses because the propagating light in the fiber is mixed over a larger number of modes which are not measured, whereas at the highest N.A. of 0.6, all modes are measured. Hence, mode mixing would decrease the collected fluorescence at lower N.A.'s but have a relatively small effect at an N.A. of 0.6. Only losses from the scattering of light from the fiber into free space modes would contribute to discrepancies between the experimental and simulation data at this high N.A. For the sensors in this study, mode mixing might be caused by the scattering from voids in the film structure although such an effect would be small because of the size of these structures (FIG. 7A), or by the transition from coated to bare to clad fiber. Mode mixing arising from the sol gel-sample interface should be minimal because of the excellent surface quality of the film (FIG. 7C).

Figure 8:
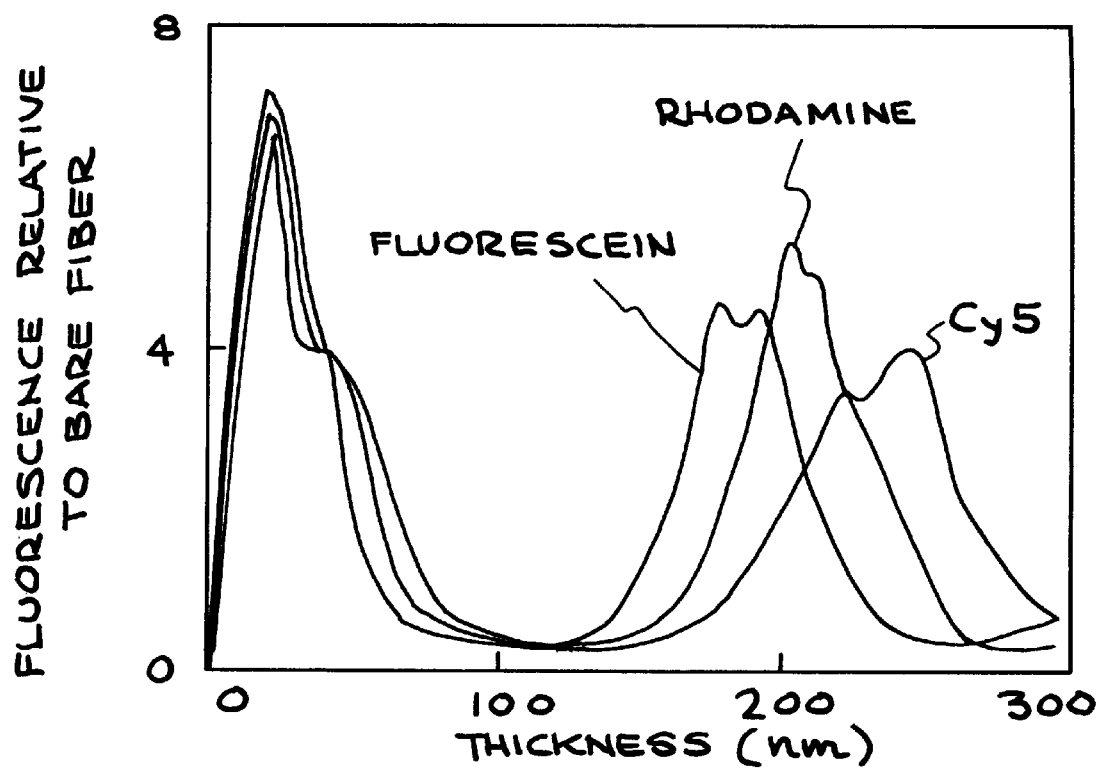
FIG. 8 displays the dependence of the collected fluorescence on the thickness of the sol-gel film for three different fluorophores emitting at different wavelengths, each having been excited at a different wavelength.

The interference effects created by the thin film impose a wavelength dependence on the collection of the fluorescence and suggest a novel application of thin films for color filtering as well as increasing collected fluorescence in fiber sensors. For example, in sensors based on fluorescence energy transfer, it would be desirable to eliminate the fluorescence of the donor from the acceptor fluorescence signal. This is usually achieved using emission filters at the collection end of the fiber, but simulations indicate that this filtering may also be achieved by taking advantage of the difference in thin-film interference effects for different dyes (FIG. 8). For example, for fluorescein-rhodamine as a donor-acceptor pair, the rhodamine signal could be preferentially amplified over that from fluorescein by selecting a film thickness of ≈220 nm. However, because $A_e$ and $E_c$ will not in general have coincidental local maxima, the amplification will be lower than its greatest value observed at smaller thicknesses.

The above described embodiment is provided as illustrative of the invention and is not considered exhaustive. Many modifications will be suggested to the skilled artisan upon review of the above disclosure. Accordingly, the invention is only limited by the fair scope of the below appended claims.

What is claimed is:

1. An optical device for more efficiently exciting and collecting fluorescence emissions, comprising:
   an optical waveguide comprising a core, a core surface, at least one material covering said core surface, and a proximal and a distal end, said material removed from one or more regions of said waveguide along a length of said waveguide distal end;
   a low porosity, thin film surrounding and coating said distal end regions thereby creating a core/thin film boundary, said thin film having a refractive index greater than said core; and a source of illumination for generating a beam of light, at least a portion of said light beam directed into said waveguide at or near said proximal end, said light essentially totally internally reflected in said core, said light propagated through said core to said distal end wherein said propagating light traverses said core/thin film boundary to create an evanescent field at said core/thin film boundary.

2. The device of claim 1 wherein said regions are located at regular or irregular intervals along said length of said distal end.

3. The device of claim 1 wherein said waveguide is a multi-mode optical fiber.

4. The device of claim 1 wherein said waveguide is a planar glass, quartz, polymer, or transparent dielectric waveguide.

5. The device of claim 1 wherein said source of illumination preferentially includes wavelengths of light capable of simulating fluorescence emission in a fluorescence molecule.

6. The device of claim 1 wherein the thin film comprises a high index of refraction, dielectric film.

7. The device of claim 6 wherein the thin film has an index of refraction between about 2.2 and about 1.7.

8. The device of claim 1 wherein the thin film is produced by dip coating or by or spin coating.

9. The device of claim 1 wherein the thin film is produced by a process selected from the list consisting of vapor phase deposition, ion implantation, diffusion, in situ polymerization, and direct chemical reaction.

10. The device of claim 8 wherein the core has a plurality of coats thereby increasing the thin film thickness.

11. The device of claim 10 wherein the thin film has a thickness of between about 15 nm and about 250 nm.

12. The device of claim 6 wherein the thin film is a sol gel film or a film produced by a sol-gel process.

13. The device of claim 12 wherein the sol gel film comprises a titanium dioxide sol film.

14. A method for enhancing the excitation and collection efficiency of a fluorescence sensor, comprising the steps of:

providing an optical waveguide having a core, a core surface and at least one material surrounding and disposed upon said core surface, said waveguide having further a distal end and a proximal end;

removing said material from one or more regions along a length of said distal end of said waveguide;

applying a coating onto said core surface of each of said regions, said coating comprising a high index of refraction thin film, said coating having an index of refraction greater than said core;

providing a light beam, at least a portion of said light beam directed into said waveguide at or near said proximal end;

propagating said light beam through said waveguide toward said distal end so as to produce an evanescent field at an external surface of said thin film coating;

placing said distal end into a liquid medium such that at least one of said regions is at least partially immersed in said medium, said medium containing molecules having fluorescent properties, said evanescent field stimulating fluorescence emission in at least some of said molecules; and collecting at least some of said fluorescence emission into one or more of said regions and propagating said emission through said waveguide to said proximal end.

15. The method of claim 14 wherein said waveguide is a multi-mode optical fiber.

16. The method of claim 14 wherein said waveguide is a planar glass, quartz, polymer, or transparent dielectric waveguide.

17. The method of claim 14 wherein said source of illumination preferentially includes wavelengths of light capable of simulating fluorescence emission in a fluorescence molecule.

18. The method of claim 14 wherein the thin film further comprises a high index of refraction, dielectric film.

19. The method of claim 18 wherein the thin film has an index of refraction between about 2.2 and about 1.7.

20. The method of claim 14 wherein the step of applying further comprises the step of dip coating or the step of spin coating.

21. The method of claim 14 wherein the thin film is produced by a process selected from the list consisting of vapor phase deposition, ion implantation, diffusion, in situ polymerization, and direct chemical reaction.

22. The method of claim 20 wherein the step of applying is repeated at least twice thereby increasing the thickness of the thin film.

23. The method of claim 22 wherein the step of applying is repeated a sufficient number of times in order to achieve a thin film thickness of between about 15 nm and about 250 nm.

24. The method of claim 14 wherein the thin film is a sol gel film or a film produced by a sol-gel process.

25. The method of claim 24 wherein the sol gel film comprises a titanium dioxide sol film.

26. A method for filtering fluorescence emission light frequencies, comprising the steps of:

providing an optical waveguide having a core, a core surface and at least one material surrounding and disposed upon said core surface, said waveguide having further a distal end and a proximal end;

removing said material in one or more regions along a length of said waveguide distal end;

applying a coating onto said core surface of each of said regions, said coating comprising a high index of refraction thin film, said coating having an index of refraction greater than said core;

adjusting the thickness of said thin film based on an interference characteristic of said waveguide and a known frequency bandwidth of light so as to preferentially detect a specific frequency bandwidth of light;

providing a light beam which includes said known frequency bandwidth incident upon a proximal end of said waveguide;

propagating said light beam through said waveguide toward said distal end so as to produce an evanescent field at an external surface of said thin film coating;

placing said distal end into a liquid medium such that at least one of said regions is at least partially immersed in said medium, said medium containing molecules having fluorescent properties, said evanescent field stimulating fluorescence emission in at least some of said molecules; and collecting at least some of said fluorescence emission into one or more of said regions and propagating said emission through said waveguide to said proximal end.

27. The device of claim 13 wherein the thickness of the titanium sol film and said stimulation frequency bandwidth are selected based on an interference characteristic of the waveguide such that light collection efficiency of said film is enhanced for light frequencies at or about a threshold light frequency thereby acting as a filter for a narrow range of light frequencies.

28. The device of claim 27 wherein said thin film thickness is adjusted so as to preferentially detect light frequencies at or about emission frequencies characteristic of a fluorescing molecule.

29. The device of claim 28 wherein the thin film thickness is adjusted within each of said regions so as to preferentially detect a number of different light frequencies, said number of frequencies corresponding to said number of said regions.

30. A method for filtering light emission frequencies, comprising the steps of:

providing an optical waveguide having a core, a core surface and at least one material surrounding and disposed upon said core surface, said waveguide having further a distal end and a proximal end;

removing said material in one or more regions along a length of said waveguide distal end;

applying a coating onto said core surface of each of said regions, said coating comprising a high index of refraction thin film, said coating having an index of refraction greater than said core;

adjusting the thickness of said thin film based on an interference characteristic of said waveguide and a known frequency bandwidth of light so as to preferentially detect a specific frequency bandwidth of light; and collecting at least some of said specific frequency bandwidths into one or more of said regions and propagating said emissions through said waveguide to said proximal end.

\* \* \* \* \*